(12) United States Patent
Bourque et al.

(10) Patent No.: US 9,579,111 B2
(45) Date of Patent: *Feb. 28, 2017

(54) OVAL TIBIA GUIDE

(71) Applicant: SMITH & NEPHEW, INC., Memphis, TN (US)

(72) Inventors: Bernard Joseph Bourque, Rehoboth, MA (US); William Richard Davis, Hingham, MA (US); Michael Charles Ferragamo, Foster, RI (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/874,962

(22) Filed: Oct. 5, 2015

(65) Prior Publication Data

US 2016/0022285 A1   Jan. 28, 2016

Related U.S. Application Data

(60) Division of application No. 14/461,973, filed on Aug. 18, 2014, now Pat. No. 9,149,285, which is a continuation of application No. 14/094,954, filed on Dec. 3, 2013, now Pat. No. 8,840,615, which is a division of application No. 13/281,130, filed on Oct. 25, 2011, now Pat. No. 8,617,168.

(60) Provisional application No. 61/406,334, filed on Oct. 25, 2010.

(51) Int. Cl.
*A61B 17/56* (2006.01)
*A61B 17/17* (2006.01)

(52) U.S. Cl.
CPC .......... *A61B 17/17* (2013.01); *A61B 17/1714* (2013.01); *A61B 17/1764* (2013.01); *A61B 17/1796* (2013.01)

(58) Field of Classification Search
CPC ............ A61B 17/1764; A61B 17/1714; A61B 17/1796
USPC .............. 606/86 R, 87–90, 96–98, 102, 104; 408/46, 241; 433/76
See application file for complete search history.

(56) References Cited

U.S. PATENT DOCUMENTS

| | | |
|---|---|---|
| 3,508,334 A | 4/1970 | Weissman |
| 4,830,023 A | 5/1989 | de Toledo et al. |
| 5,207,753 A | 5/1993 | Badrinath |
| 5,613,971 A | 3/1997 | Lower et al. |
| 5,681,320 A * | 10/1997 | McGuire ............ A61B 17/0401 606/104 |
| 5,716,360 A | 2/1998 | Baldwin et al. |
| 6,019,767 A | 2/2000 | Howell |

(Continued)

FOREIGN PATENT DOCUMENTS

RU   2125844 C1   2/1999
RU   2241394 C2   12/2004

*Primary Examiner* — Tatiana Nobrega
*Assistant Examiner* — Marcela I Shirsat
(74) *Attorney, Agent, or Firm* — Burns & Levinson LLP; Joseph M. Maraia (57) ABSTRACT

A guide apparatus having a body having a central axis defined therethrough and a first channel and a second channel formed therethrough, a handle coupled to the body, the handle having a locking mechanism configured to prevent movement of the body relative to the handle in a first direction along the central axis of the body, and an arm coupled to the handle, the arm configured to engage at least a portion of a bone.

15 Claims, 7 Drawing Sheets

(56) References Cited

U.S. PATENT DOCUMENTS

| | | | |
|---|---|---|---|
| 6,022,356 | A | 2/2000 | Noyes et al. |
| 6,120,511 | A | 9/2000 | Chan |
| 6,210,415 | B1 | 4/2001 | Bester |
| 6,918,916 | B2 | 7/2005 | Gobel et al. |
| 8,343,161 | B2 * | 1/2013 | Re .................... A61B 17/1714 606/89 |
| 8,523,872 | B2 | 9/2013 | Ek |
| 8,840,615 | B2 * | 9/2014 | Bourque ............ A61B 17/1714 606/103 |
| 2001/0053934 | A1 | 12/2001 | Schmieding |
| 2003/0009218 | A1 | 1/2003 | Boucher et al. |
| 2003/0083688 | A1 | 5/2003 | Simonson |
| 2006/0155290 | A1 * | 7/2006 | Shino ................. A61B 17/1604 606/86 R |
| 2006/0195112 | A1 | 8/2006 | Ek |
| 2007/0118136 | A1 | 5/2007 | Ek |
| 2010/0068233 | A1 | 3/2010 | Bangera et al. |
| 2010/0249930 | A1 | 9/2010 | Myers |
| 2011/0313478 | A1 | 12/2011 | Herdrich et al. |

* cited by examiner

OVAL TIBIA GUIDE

CROSS REFERENCE TO RELATED APPLICATIONS

This application is a divisional of U.S. patent application Ser. No. 14/461,973 filed Aug. 18, 2014, which is a continuation of U.S. patent application Ser. No. 14/094,954 filed Dec. 3, 2013 entitled OVAL TIBIA GUIDE, which is a divisional of U.S. patent application Ser. No. 13/281,130 filed Oct. 25, 2011 entitled OVAL TIBIA GUIDE now U.S. Pat. No. 8,617,168, which claims benefit of the priority of U.S. Provisional Application No. 61/406,334 filed Oct. 25, 2010 entitled OVAL TIBIA GUIDE.

BACKGROUND

Damaged ligaments, cartilage and tendons in joints are not an uncommon occurrence, particularly with today's emphasis on physical activity and conditioning. One of the joints which requires particular skill and presents particular difficulties in repairing is the knee joint.

Numerous improvements in repairing damage to knee joints have been made over the years, and some of the major advances involve endoscopic techniques and arthroscopic procedures. Arthroscopic surgery is particularly useful in excising or repairing damaged knee cartilage.

Endoscopic techniques have also been developed for use in repair and reconstruction of damaged anterior cruciate ligaments (ACL) and posterior cruciate ligaments (PCL). When the ACL in particular has ruptured and is nonrepairable, it is usually replaced in young adults and the knee reconstructed through use of grafts (biological or synthetic).

The function of the real cruciate ligaments is complicated. The ACL and PCL are three-dimensional structures with broad attachments and a continuum of fibers. These fibers are of different lengths, have different attachment sites, and are under different tensions. Although many current substitutes for cruciate ligaments have not duplicated the complex orientation and operation of normal ACLs, they operate the best and mimic the normal ACL operation the best when they are placed isometrically. "Isometrically" positioned means that the length of the substitute ligament will not change during annular movement of the tibia relative to the femur; the distance between the affixed ends of the ligament remains a constant. Isometric placement maximizes the number of fibers that can be taut throughout the range of motion of the knee and allows for early knee motion without generating high ligament strains.

Correct isometric positioning of the ACL graft thus is an important factor for a successful operation. Correct isometric placement reproduces corresponding femoral and tibial anatomic attachment sites and will allow an ACL graft to mimic the normal ACL. Isometrically placed grafts provide the most stable knees. Non-isometric graft placement can result in plastic deformation of the ACL substitute, postoperative laxity, abnormal kinematics, or failure of fixation.

The importance of accurate placement of an ACL substitute is shown by the fact that graft placements sometimes only several millimeters apart produce significantly different strains in the cruciate substitute. A placement of the ACL origin or insertion which is too anteriorly placed in the knee joint results in a ligament that is taut in flexion, but lax in extension. Posterior placement causes the ligament to be taut in extension, but lax in flexion. Only isometric placement provides stability throughout the range of motion.

SUMMARY

According to one aspect, there is provided a guide apparatus having a body having a central axis defined therethrough and a first channel and a second channel formed therethrough, a handle coupled to the body, the handle having a locking mechanism configured to prevent movement of the body relative to the handle in a first direction along the central axis of the body, and an arm coupled to the handle, the arm configured to engage at least a portion of a bone.

According to another aspect, there is provided a method of guiding at least one guidewire into a bone including providing a guide apparatus having a body, a handle, and an arm, the body having a central axis defined therethrough, and the handle having a locking mechanism, engaging at least a portion of the arm with the bone, engaging at least a portion of the body with the bone, disposing at least one guidewire into at least one channel formed through the body, and drilling the at least one guidewire into the bone.

DETAILED DESCRIPTION

The disclosures of U.S. patent application Ser. No. 14/094,954 filed Dec. 3, 2013 entitled OVAL TIBIA GUIDE, U.S. patent application Ser. No. 13/281,130 filed Oct. 25, 2011 entitled OVAL TIBIA GUIDE, and U.S. Provisional Application No. 61/406,334 filed Oct. 25, 2010 are hereby incorporated herein by reference in their entirety.

The following is directed to various exemplary embodiments of the disclosure. Although one or more of these embodiments may be preferred, the embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment.

Certain terms are used throughout the following description and claims refer to particular features or components. As those having ordinary skill in the art will appreciate, different persons may refer to the same feature or component by different names. This document does not intend to distinguish between components or features that differ in name but not function. The figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first component is coupled to a second component, that connection may be through a direct connection, or through an indirect connection via other components, devices, and connections. Further, the terms "axial" and "axially" generally mean along or substantially parallel to a central or longitudinal axis, while the terms "radial" and "radially" generally mean perpendicular to a central, longitudinal axis.

Figure 1:
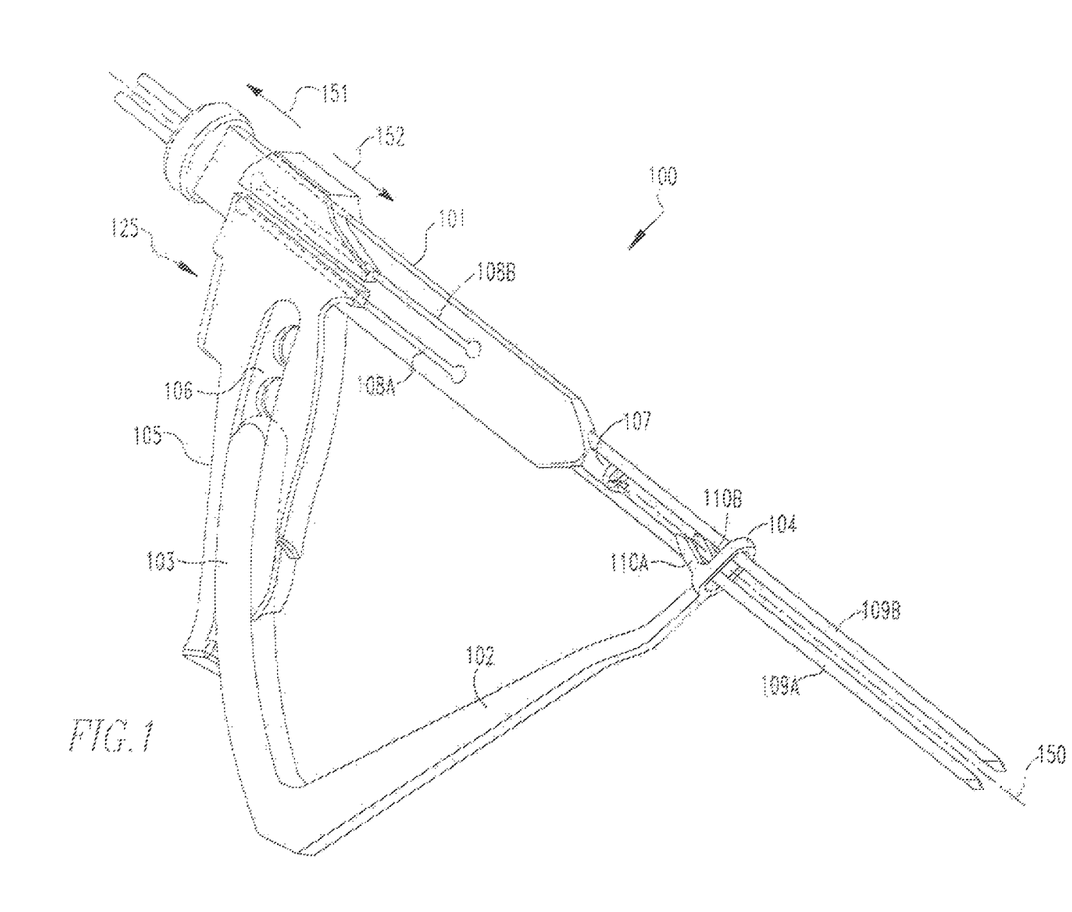
FIG. 1 is a perspective view of a guide apparatus, in accordance with embodiments disclosed herein.

Referring to FIG. 1, a perspective view of a guide apparatus 100, according to embodiments disclosed herein, is shown. In one or more embodiments, the guide apparatus 100 may be a tibia oval guide. In other words, in one or more embodiments, the guide apparatus 100 may be used to engage a tibia and may be used to help form a substantially oval-shaped tunnel in a bone, e.g., a tibia. For example, as will be explained further below, the guide apparatus 100 may be used to precisely guide at least one guidewire into, and through, a specific location of a bone. Accurately positioning at least one guidewire into, and through, a specific location of a bone may allow a substantially oval-shaped tunnel to be formed through a specific location of the bone. In other words, in one or more embodiments, the specifically placed guidewires may help guide any means of forming tunnels in bones known in the art form one or more tunnels through the bone over and along the guidewires. Further, in one or more embodiments, the one or more holes formed over and along the guidewires through the bone may overlap and may form a single oblong or substantially oval-shaped tunnel through the bone.

In one or more embodiments, the guide apparatus 100 may include a body 101 having a central axis 150 defined therethrough and a first channel 108A and a second channel 108B formed therethrough. In one or more embodiments, each of the first channel 108A and the second channel 108B may be configured to receive a guidewire, i.e., a first guidewire 109A or a second guidewire 109B. In one or more embodiments, each of the first channel 108A and the second channel 108B may be configured to receive either the first guidewire 109A or the second guidewire 109B. However, in one or more embodiments, the first channel 108A may be configured to receive the first guidewire 109A, and the second channel 108B may be configured to receive the second guidewire 109B. Alternatively, in one or more embodiments, the first channel 108A may be configured to receive the second guidewire 109B, and the second channel 108B may be configured to receive the first guidewire 109A.

Those having ordinary skill in the art will appreciate that the guidewires 109A, 109B may be substantially identical guidewires. Alternatively, those having ordinary skill in the art will appreciate that the dimensions of the first guidewire 109A may be different from the dimensions of the second guidewire 109B. For example, in one or more embodiments, the first guidewire 109A may be longer than the second guidewire 109B and vice versa. Further, in one or more embodiments, the first guidewire 109A may have a larger diameter than the second guidewire 109B and vice versa.

In one or more embodiments, the guidewires 109A, 109B may be formed from any substantially rigid material known in the art. For example, each of the first guidewire 109A and the second guidewire 109B may be made of, or formed from, a plastic or a metal, such as Nitinol, or any combination of materials known in the art.

In one or more embodiments, the body 101 may include a projection 107 that is configured to engage with a bone (not shown). In one or more embodiments, a surface of the projection 107 that is configured to engage with the bone, i.e., a surface of the projection that is farthest from the rest of the body 101, may be a textured surface. In other words, a surface of the projection 107 that is configured to engage with the bone may include one or more features that may help stabilize, or otherwise enhance, engagement between the body 101 and the bone. For example, the surface of the projection 107 that is configured to engage with the bone may include an array of teeth, arranged in a star-shaped pattern, having a plurality of smaller projections that may help stabilize contact, or engagement, between the body 101 and the bone.

In one or more embodiments, the projection 107 may be formed from the same material(s) as the body 101 of the guide apparatus 100. Alternatively, in one or more embodiments, the projection 107 may be formed from a different material as the body 101 of the guide apparatus 100. For example, in one or more embodiments, the projection 107 may be a projection of the body 101, and both the body 101 and the projection 107 may be formed from any substantially rigid material, or combination of materials, known in the art, including any known plastics, metals, or ceramics known in the art. Alternatively, in one or more embodiments, the projection 107 may be coupled, or formed onto, the body 101, and the body 101 may be formed from a plastic and the projection 107 may be formed from any other substantially rigid material known in the art, such as a metal or a combination of materials.

Further, in one or more embodiments, the guide apparatus 100 may include a handle 105 coupled to the body 101, the handle 105 having a locking mechanism 125 configured to prevent movement of the body 101 relative to the handle 105 in a first direction, e.g., in the direction of arrow 151, along the central axis 150 of the body 101. As will be discussed further below, in one or more embodiments, the locking mechanism 125 is movable between an engaged position and a disengaged position. In one or more embodiments, the body 101 may be movable, relative to the handle 105, along the central axis 150 of the body 101 in the first direction, e.g., in the direction of arrow 151, and/or in the second direction, e.g., in the direction of the arrow 152. In one or more embodiments, in the engaged position, the locking mechanism 125 may only allow the body 101 to move, relative to the handle 105, in the second direction. In other words, in the engaged position, the locking mechanism 125 may prevent movement, or displacement, of the body 101, relative to the handle 105, in the first direction. In the disengaged position, the locking mechanism 125 may allow movement, or displacement, of the body 101, relative to the handle 105, in both the first direction and the second direction.

Further, in one or more embodiments, the handle 105 may include a slot 106 formed thereon, in which a proximal end 103 of the arm 102 may be engaged with the slot 106 and may be slidable within the slot 106. In one or more embodiments, the slot 106 may be substantially linear. Alternatively, in one or more embodiments, the slot 106 may be curved or arced. As will be discussed below, one or more portions of the arm 102 may be curved or arced. In one or more embodiments, the slot 106 may be configured to receive at least a portion of the arm 102, e.g., the curve or arc of the slot 106 may be substantially similar, or identical, to a curved or arced portion of the arm 102 that may be received within the slot 106.

In one or more embodiments, a position of the arm 102 relative to the handle 106 may be lockable within the slot 106. In other words, in one or more embodiments, the arm 102 may be slidable within the slot 106, e.g., substantially along the length of the handle 105. However, in one or more embodiments, the arm 102 may include a feature or mechanism that may lock the arm 102 within the slot 106 of the handle 105, or prevent relative movement of the arm 102 relative to the handle 105, in order to secure a position of the arm 102. In one or more embodiments, one or more surfaces of the arm 102 that may contact or engage the slot 106 may be textured surfaces that may help engage, or lock, the arm 102 within the slot 106. Alternatively, one or more surfaces of the slot 106 may be textured surfaces that may help engage, or lock the arm 102 within the slot 106. In one or more embodiments, both the surfaces of the arm 102 and surfaces of the slot 106 may be textured surfaces to promote engagement between the arm 102 and the slot 106. Alternatively, in one or more embodiments, the arm 102 may include any other means known in the art, such as a releasable locking mechanism, that may be engaged or disengaged within the slot 106 in order to lock the position of the arm 102 within the slot 106.

In one or more embodiments, the guide apparatus 100 may include an arm 102 coupled to the handle 105, the arm 102 configured to engage at least a portion of a bone (not shown). In one or more embodiments, a distal end of the arm 102 may include a guide loop 104 configured to receive at least two guidewires, e.g., the first guidewire 109A and the second guidewire 109B. In one or more embodiments, the guide loop 104 may provide an intended target region, through which the guidewires 109A, 109B may be intended to be disposed.

For example, as discussed above, one object of the guide apparatus 100 may be used to accurately position and/or precisely guide at least one guidewire into, and through, a specific location of a bone. The arm 102 of the guide apparatus 100 may be configured such that the position of the guide loop 104 may identify the intended exit position of the guidewires, e.g. the guidewires 109A, 109B, through the bone. In one or more embodiments, the channels 108A, 108B may be formed in parallel on either side, e.g., about, the projection 107. Further, in one or more embodiments, both the projection 107 and a center of the guide loop 104 may be aligned along the central axis 150 of the body 101. As such, in one or more embodiments, at least one guidewire may be disposed through the channels 108A, 108B, through the bone, and at least partially through the guide loop 104 of the arm 102.

In other words, as will be discussed in more detail below, the distal end of the arm 102 may be engaged with the bone such that the guide loop 104 is positioned substantially about the desired exit point(s) of the guidewires. Further, the body 101 of the guide apparatus 100 may be moved in a second direction, e.g., in the direction of arrow 152, along the central axis 150 of the body 101 until the projection 107 contacts, or is engaged with, the bone such that the projection 107 is positioned substantially about the desired entry point(s) of the guidewires. As such, the entry points and exit points of the guidewires may be accurately identified and targeted on the bone before disposing the guidewires into, or through, the bone.

In one or more embodiments, the distal end of the arm 102 may include at least one protrusion, i.e., a first protrusion 110A and a second protrusion 110B, in which the at least one protrusion is configured to engage with the bone. For example, in one or more embodiments, each of the first protrusion 110A and the second protrusion 110B may have a sharp, or pointed, end that may assist with, or promote, engagement between the arm 102 and the bone. In one or more embodiments, each of the first protrusion 110A and the second protrusion 110B may not necessarily be sharp or pointed and may still be configured to engage with the bone or a surface of the bone. For example, in one or more embodiments, at least a portion of each of the first protrusion 110A and the second protrusion 110B may break a surface of the bone and be, at least partially, disposed within the bone. In one or more embodiments, the at least one protrusion, e.g., the first protrusion 110A and the second protrusion 110B, may extend substantially in a perpendicular, or orthogonal, direction from the arm 102 or from a plane of the guide loop 104 formed on a distal end of the arm 102.

As discussed above, in one or more embodiments, at least a portion of the arm 102, e.g., the proximal end 103 of the arm 102, may be curved or arced. Further, in one or more embodiments, at least a portion of the arm 102 may be bent. For example, as shown in FIG. 1, the arm 102 is bent. In one or more embodiments, the arm 102 may be bent to a 45 degree angle. However, those having ordinary skill in the art will appreciate that the arm 102 may not necessarily need to be bent at all. Further, those having ordinary skill in the art will appreciate that, in one or more embodiments, at least a portion of the arm 102 may be bent between 1 degree and 179 degrees.

In one or more embodiments, the at least one protrusion, e.g., the first protrusion 110A and the second protrusion 110B, may be formed from the same material as the arm 102 of the guide apparatus 100. Alternatively, in one or more embodiments, the at least one protrusion may be formed from a different material as the arm 102 of the guide apparatus 100. For example, in one or more embodiments, the at least one protrusion may be projections of the arm 102, and both the arm 102 and the at least one protrusion may be formed from any substantially rigid material, or combination of materials, known in the art, including any known plastics, metals, or ceramics known in the art. Alternatively, in one or more embodiments, the at least one protrusion may be coupled to, or formed onto, the arm 102, and the arm 102 may be formed from a metal and the at least one protrusion may be formed from any other substantially rigid material known in the art, such as a plastic or a combination of materials.

Figure 2:
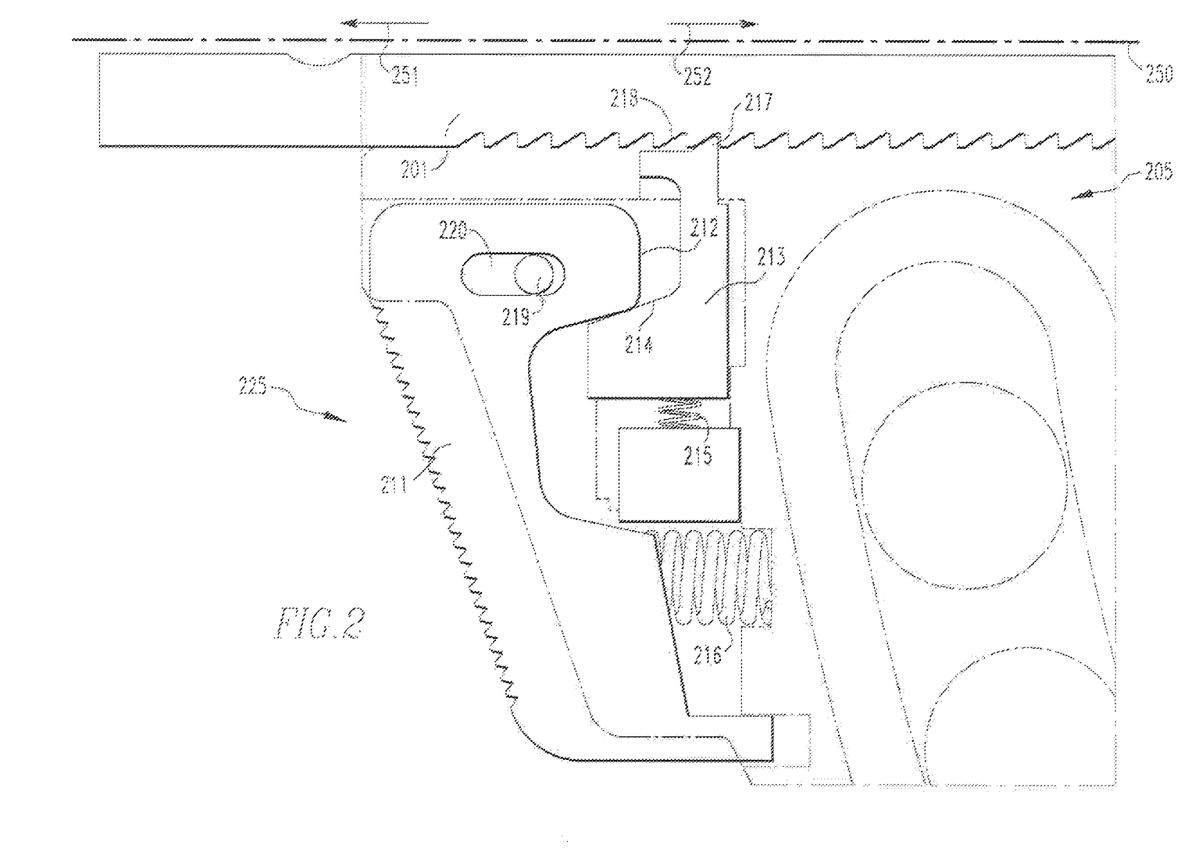
FIG. 2 is a cross-sectional view of a locking mechanism, in accordance with embodiments disclosed herein.

Referring to FIG. 2, a cross-sectional view of a locking mechanism 225, according to embodiments disclosed herein, is shown. In one or more embodiments, the locking mechanism 225 may include a trigger 211 and a movable piece 213. Further, in one or more embodiments, a body 201 may have a central axis 250 defined therethrough and may include a plurality of locking threads 218, which may be ratchet threads, serrations, or a series of angled grooves, formed thereon. The locking threads 218 may be configured to engage with a locking portion 217 of the movable piece 213.

In one or more embodiments, the locking portion 217 of the movable piece 213 may be a projection, or protrusion, from the movable piece 213. In one or more embodiments, the locking portion 217 may be configured to engage with the locking threads 218 of the body 201. For example, in one or more embodiments, the locking portion 217 of the movable piece 213 may be an angled protrusion of the movable piece 213, e.g., may have a slanted, sloped, or inclined face, that may be configured to engage with ratchet threads, serrations, or a series of angled grooves, i.e., the locking threads 218.

Those having ordinary skill in the art will appreciate that the locking mechanism 225, according to embodiments disclosed herein, may include one or more movable pieces, e.g., the movable piece 213, which may include one or more locking portions, e.g., the locking portion 217. For example, in one or more embodiments, the locking mechanism may include one, two, three, four, or more movable pieces, each having one, two, three, four, or more locking portions configured to engage with one or more locking threads of the body.

In one or more embodiments, the trigger 211 may have a portion 212 that may be configured to engage, or interact, with the movable piece 213. In one or more embodiments, the movable piece 213 may have a slanted, or inclined, face 214 that is configured to engage, or interact with, the portion 212 of the trigger 211. As such, as the trigger 211 is moved in a direction toward the movable piece 213, the portion 212 of the trigger 211 may become engaged with the inclined surface 214 of the movable piece 213. In one or more embodiments, as the portion 212 of the trigger 211 becomes more engaged with the inclined face 214 of the movable piece 213, i.e., as the portion 212 of the trigger 211 moves up the inclined face 214 of the movable piece 213, this may cause the movable piece 213 to move in a downward direction, i.e., in a direction away from the body 201. In one or more embodiments, moving the movable piece 213 in the downward direction may cause the locking portion 217 of the movable piece 213 to disengage from the locking threads 218 of the body 201.

As discussed above, the locking mechanism 225 is movable between an engaged position and a disengaged position. In one or more embodiments, the body 201 may be movable, relative to the handle 205, along the central axis 250 of the body 201 in the first direction, i.e., in the direction of arrow 251, and/or in the second direction, i.e., in the direction of the arrow 252. In one or more embodiments, each of the first direction and the second direction may be along, or substantially parallel to, the central axis 250 of the body 201.

In one or more embodiments, in the engaged position, the locking mechanism 225 may only allow the body 201 to move, relative to the handle 205, in the second direction. In other words, in the engaged position, the locking mechanism 225 may prevent movement, or displacement, of the body 201, relative to the handle 205, in the first direction, but may allow movement of the body 201, relative to the handle 205, in the second direction.

For example, when the locking mechanism 225 is in the engaged position, the locking portion 217 of the movable piece 213 may be engaged with at least one of the plurality of locking threads 218 of the body 201. In one or more embodiments, the plurality of locking threads 218 may be structured, or configured, to allow movement of the body 201 in the second direction, i.e., in the direction of the arrow 252, relative to the handle 205, while the locking portion 217 of the movable piece 213 is engaged with at least one of the plurality of locking threads 218. Further, in one or more embodiments, the plurality of locking threads 218 may be structured, or configured, to prevent movement of the body 201 in the first direction, i.e., in the direction of the arrow 251, relative to the handle 205 while the locking portion 217 of the movable piece 213 is engaged with at least one of the plurality of locking threads 218.

In the disengaged position, the locking mechanism 225 may allow movement, or displacement, of the body 201, relative to the handle 205, in both the first direction and the second direction. For example, as discussed above, forcing, or moving, the trigger 211 in the direction toward the movable piece 213 may cause the movable piece 213 to move in a downward direction, i.e., in a direction away from the body 201, as a result of the engagement between the inclined surface 214 of the movable piece 213 and the portion 212 of the trigger 211. In one or more embodiments, the locking portion 217 of the movable piece 213 may become disengaged from the plurality of locking threads 218 as the movable piece 213 is moved in the downward direction. Once the locking portion 217 of the movable piece 213 is disengaged from the plurality of locking threads 218 of the body 201, the body 201 may be free to move, relative to the handle 205, in both the first direction and the second direction, represented by arrows 251, 252, respectively.

In one or more embodiments, the locking mechanism 225 may include at least one biasing member configured to bias the locking mechanism 225 toward the engaged position. Those having ordinary skill in the art will appreciate that a biasing member, according to embodiments disclosed herein, may be any device or mechanism that is configured to exert a force on, or bias, an article, e.g., the trigger 211 and/or the movable piece 213, in a given direction. For example, in one or more embodiments, the biasing member may be a spring.

In one or more embodiments, the locking mechanism 225 may include a first spring 215 engaged with a portion of the handle 205 and the movable piece 213. In one or more embodiments, the first spring 215 may exert a force on, or bias, movable piece 213 in a direction that is toward the body 201, i.e., in an upward direction such that the lockable portion 217 of the movable piece 213 may engage with at least one of the plurality of locking threads 218 of the body 201. As such, in one or more embodiments, the first spring 215 may bias the locking mechanism 225 toward the engaged position.

In one or more embodiments, the locking mechanism 225 may include a second spring 216 engaged with a portion of the handle 205 and the trigger 211. In one or more embodiments, the second spring 216 may exert a force on, or bias, the trigger 211 in the first direction, e.g., in a direction that is away from the movable piece 213, i.e., in direction of the arrow 251. As discussed above, as the trigger 211 moves in a direction toward the movable piece 213, this may cause the movable piece 213 to move in a downward direction, i.e., in a direction away from the body 201, as a result of the engagement between the inclined surface 214 of the movable piece 213 and the portion 212 of the trigger 211. Conversely, in one or more embodiments, as the trigger 211 moves in a direction that is away from the movable piece 213, the less force the portion 212 of the trigger 211 may impose on the inclined surface 214 of the movable piece 213. In turn, a reduced force imposed on the movable piece 213 by the trigger 211 may allow the movable piece 213 to move in an upward direction, i.e., a direction toward the body 201, as a result of the biasing force imposed by the first spring 215, as discussed above. As such, in one or more embodiments, the second spring 216 may bias the locking mechanism 225 toward the engaged position.

Those having ordinary skill in the art will appreciate that a first spring 215 and a second spring 216 may not necessarily be required to bias the locking mechanism 225 toward the engaged position. For example, in one or more embodiments, the locking mechanism 225 may include one, three, four, five, or more biasing members that may be configured to bias the locking mechanism 225 toward the engaged position.

In one or more embodiments, the locking mechanism 225 may include a pin 219, which may be disposed within a slot 220 formed in the trigger 211. In one or more embodiments, the extent to which the trigger 211 may move in the second direction, toward the movable piece 213, may be limited by the pin 219, as the pin 219 may abut at least a portion of the slot 220 and prevent the trigger 211 from moving further in the second direction.

Figure 3A:
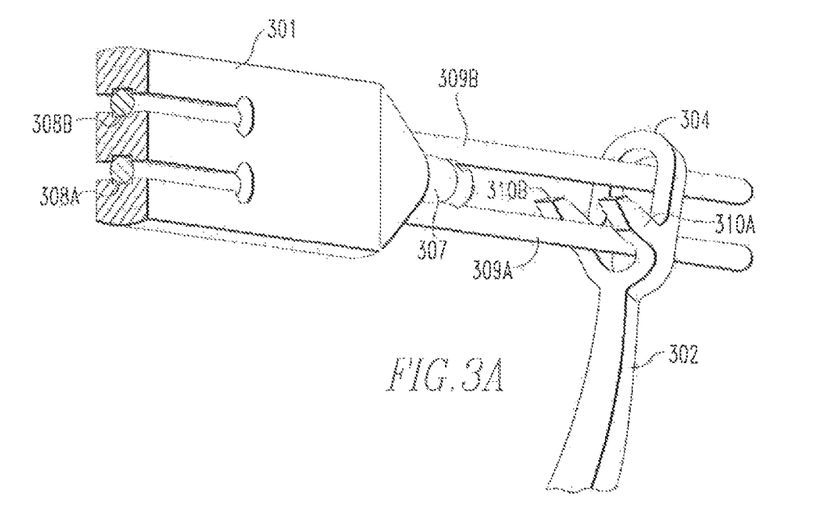
FIGS. 3A-3B are multiple views of a distal end of an arm of a guide apparatus having guidewires disposed therethrough, in accordance with embodiments disclosed herein.
Figure 3B:
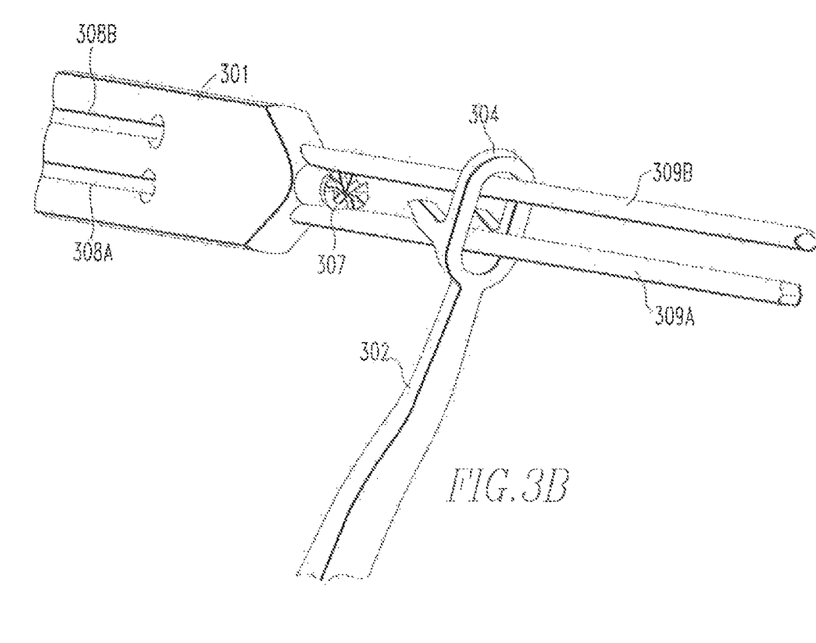

Referring now to FIGS. 3A-3B, multiple close-up views of a distal end of an arm 302 of a guide apparatus having guidewires 309A, 309B disposed therethrough, according to embodiments disclosed herein, are shown. As shown, the guide apparatus may include a body 301, the body 301 having a first channel 308A and a second channel 308B formed therethrough. As discussed above, each of the first channel 308A and the second channel 308B may be configured to receive a guidewire, i.e., guidewires 309A, 309B. In one or more embodiments, each of the first channel 308A and the second channel 308B may be configured to receive either the first guidewire 309A or the second guidewire 309B. However, in one or more embodiments, the first channel 308A may be configured to receive the first guidewire 309A, and the second channel 308B may be configured to receive the second guidewire 309B. Alternatively, in one or more embodiments, the first channel 308A may be configured to receive the second guidewire 309B, and the second channel 308B may be configured to receive the first guidewire 309A.

As shown, a cross-section of each of the first channel 308A and the second channel 308B may be square-shaped cross-section. However, those having ordinary skill in the art will appreciate that the cross-section of each of the first channel 308A and the second channel 308B may be configured to receive a guidewire of any shape known in the art and may be formed of any shape known in the art. For example, a cross-section of each of the first channel 308A and the second channel 308B may be square, triangular, hexagonal, circular, elliptical, or any other shape known in the art. Similarly, those having ordinary skill in the art will appreciate that a cross-section of a guidewire, according to embodiments disclosed herein, may be of any shape known in the art. For example, a cross-section of each of the first guidewire 309A and the second guidewire 309B may be square, triangular, hexagonal, circular, elliptical, or any other shape known in the art.

As discussed above, those having ordinary skill in the art will appreciate that the guidewires 309A, 309B may be substantially identical guidewires. Alternatively, those having ordinary skill in the art will appreciate that the dimensions of the first guidewire 309A may be different from the dimensions of the second guidewire 309B. For example, in one or more embodiments, the first guidewire 309A may be longer than the second guidewire 309B and vice versa. Further, in one or more embodiments, the first guidewire 309A may have a larger diameter than the second guidewire 309B and vice versa.

Further, as discussed above, in one or more embodiments, the guidewires 309A, 309B may be formed from any substantially rigid material known in the art. For example, each of the first guidewire 309A and the second guidewire 309B may be made of, or formed from, a plastic or a metal, such as Nitinol, or any combination of materials known in the art. Furthermore, in one or more embodiments, a distal end, e.g., an end that may contact a bone, of each of the guidewires 309A, 309B may be sharpened, or pointed, ends that may assist with the disposal of each of the guidewires 309A, 309B into the bone. However, those having ordinary skill in the art will appreciate that the distal end of each of the guidewires 309A, 309B may not necessarily be sharpened, or pointed, ends. For example, in one or more embodiments, the distal end of each of the guidewires 309A, 309B may be a flat or rounded end.

In one or more embodiments, the body 301 may include a projection 307 that is configured to engage with a bone (not shown). In one or more embodiments, a surface of the projection 307 that is configured to engage with the bone, i.e., a surface of the projection that is farthest from the rest of the body 301, may be a textured surface. In other words, a surface of the projection 307 that is configured to engage with the bone may include features that may help stabilize, or otherwise enhance, engagement between the body 301 and the bone. For example, the surface of the projection 307 that is configured to engage with the bone may include an array of teeth, arranged in a star-shaped pattern, having a plurality of smaller projections that may help stabilize contact, or engagement, between the body 301 and the bone.

As discussed above, in one or more embodiments, the projection 307 may be formed from the same material as the body 301 of the guide apparatus. Alternatively, in one or more embodiments, the projection 307 may be formed from a different material as the body 301 of the guide apparatus. For example, in one or more embodiments, the projection 307 may be a projection of the body 301, and both the body 301 and the projection 307 may be formed from any substantially rigid material, or combination of materials, known in the art, including any known plastics, metals, or ceramics known in the art. Alternatively, in one or more embodiments, the projection 307 may be coupled, or formed onto, the body 301, and the body 301 may be formed from a plastic and the projection 307 may be formed from any other substantially rigid material known in the art, such as a metal or a combination of materials.

In one or more embodiments, the distal end of the arm 302 may include at least one protrusion, i.e., a first protrusion 310A and a second protrusion 310B, in which the at least one protrusion is configured to engage with the bone. For example, in one or more embodiments, each of the first protrusion 310A and the second protrusion 310B may have a sharp, or pointed, end that may assist with, or promote, engagement between the arm 302 and the bone. In one or more embodiments, each of the first protrusion 310A and the second protrusion 310B may not necessarily be sharp or pointed, and may still be configured to engage with the bone or a surface of the bone. For example, in one or more embodiments, at least a portion of each of the first protrusion 310A and the second protrusion 310B may break a surface of the bone and be, at least partially, disposed within the bone.

Those having ordinary skill in the art will appreciate that one, three, four, or more protrusions may be formed on the arm 302 and may be configured to assist with, or promote, engagement between the arm 302 and the bone. Further, in one or more embodiments, instead of one or more protrusions, a surface of the arm 302 that may be engaged with the bone may be a textured surface, as described above with regard to the projection 307.

In one or more embodiments, the distal end of the arm 302 may include a guide loop 304 configured to receive at least two guidewires, e.g., the first guidewire 309A and the second guidewire 309B. In one or more embodiments, the guide loop 304 may provide an intended target region, through which the guidewires 309A, 309B may be intended to be disposed.

According to another aspect, there is provided a method of guiding at least one guidewire into a bone. According to one or more aspects, the method may include providing a guide apparatus having a body, a handle, and an arm, the body having a central axis defined therethrough, and the handle having a locking mechanism, engaging at least a portion of the arm with the bone, engaging at least a portion of the body with the bone, disposing at least one guidewire into at least one channel formed through the body, and drilling the at least one guidewire into the bone.

Figure 4A:
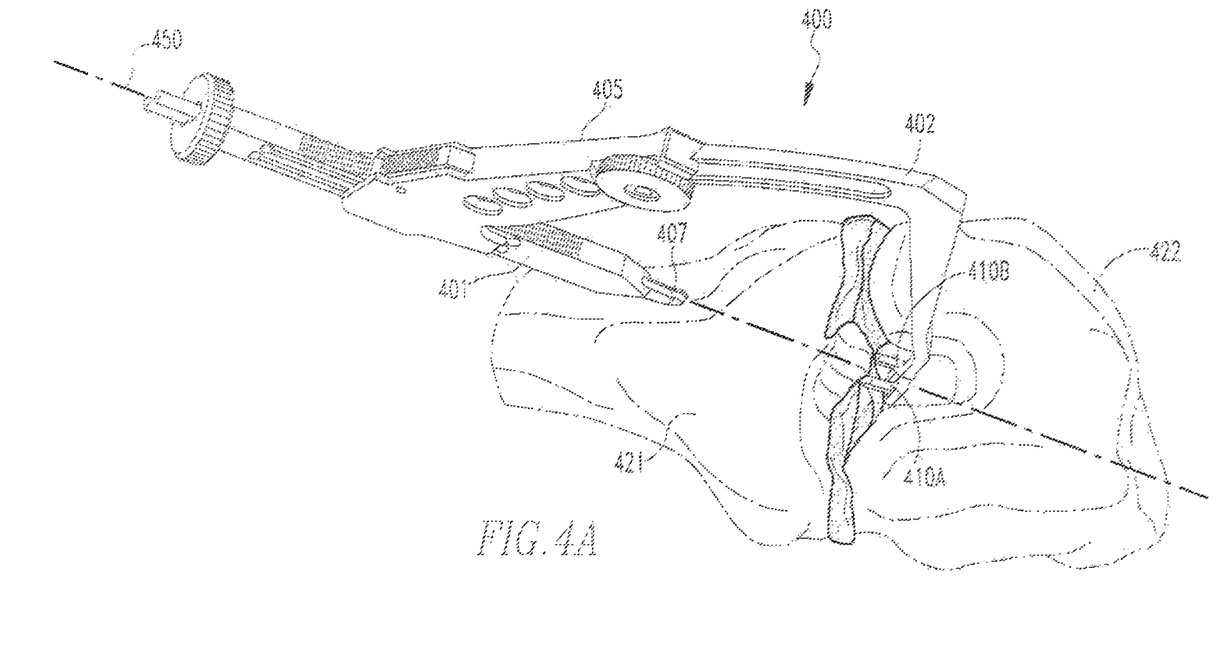
FIGS. 4A-4B are multiple views of a guide apparatus engaged with a bone, in accordance with embodiments disclosed herein.
Figure 4B:
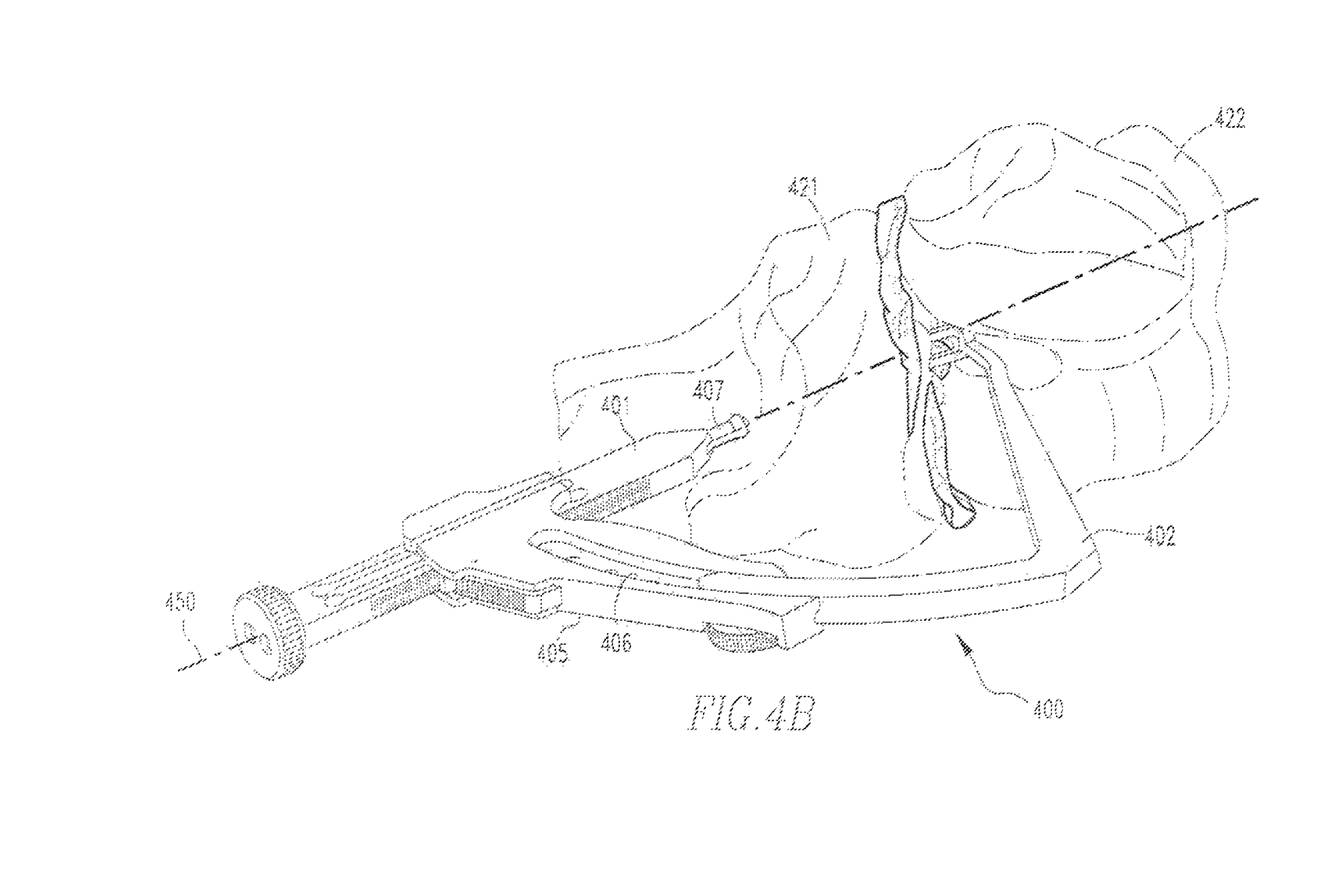

Referring to FIGS. 4A-4B, multiple views of a guide apparatus 400 engaged with a bone 421, according to embodiments disclosed herein, are shown. According to one or more aspects, the guide apparatus 400 may include a body 401, a handle 405, and an arm 402, the body 401 having a central axis 450 formed therethrough, and the handle having a locking mechanism (not shown).

According to one or more aspects, the arm 402 of the guide apparatus 400 may be engaged with a first side of the bone 421. As discussed above, in one or more embodiments, a distal end of the arm 402 may include at least one protrusion, in which the at least one protrusion is configured to engage with the bone. As such, according to one or more aspects, the at least one protrusion of the arm 402 may engage with the first side of the bone 421. However, as discussed above, the arm 402 may not necessarily include at least one protrusion in order to engage with the first side of the bone 421. For example, according to one or more aspects, a surface of the arm 402 that may engage with the first side of the bone 421 may be a textured surface, which may help stabilize contact, or engagement, between the arm 402 and the bone 421.

Further, according to one or more aspects, the body 401 may include a projection 407 that may be configured to engage with a second side of the bone 421. According to one or more aspects, engaging at least a portion of the body 401 with the bone 421 may include engaging the projection 407 with the bone 421, e.g., with the second side of the bone 421. According to one or more aspects, as the arm 402 and the handle 405 may be substantially rigid, engaging at least a portion of the body 401 with the bone 421 may include moving the body 401, relative to the handle 405, along the central axis 450 and toward the second side of the bone 421.

According to one or more aspects, both the projection 407 and the distal end of the arm 402, e.g., a center of a guide loop (not shown) formed on the distal end of the arm 402, may be substantially aligned with the central axis 450 of the body 401. Further, as discussed above, a first channel (not shown) and a second channel (not shown) may be formed through the body 401 and may be configured to receive guidewires (not shown). According to one or more aspects, the first channel may be substantially parallel to the second channel and the channels may be formed on either side of the projection 407. This structure, or configuration, may allow guidewires to be guided in a direction that is substantially parallel to the central axis 450 of the body 401, toward the bone 421 and toward the distal end of the arm 402.

According to one or more aspects, engaging the body 401 with the bone 421 may include moving the locking mechanism from an engaged position into a disengaged position and moving the body 401 toward the bone 421, along the central axis 450 of the body 401, until at least a portion of the body 401 is engaged with the bone 401.

For example, referring back to FIG. 2 described above, the trigger 211 may be moved, or displaced, in the second direction, i.e., in the direction of arrow 252, which may cause the locking portion 217 of the movable piece 213 to disengage from the locking threads 218 of the body 201. According to one or more aspects, once the locking portion 217 of the movable piece 213 is disengaged from the locking threads 218 of the body 201, the locking mechanism 225 is in the disengaged position. Once the locking mechanism 225 is in the disengaged position, the body 201 may be free to move in both the first direction and the second direction relative to the handle 205. However, as discussed above, having the locking mechanism 225 in the engaged position may allow movement, or displacement, of the body 201 only in the second direction, while preventing movement, or displacement, of the body 201 in the first direction relative to the handle 205.

For example, according to one or more aspects, moving the body 201 in the second direction, i.e., in the direction of the arrow 252, e.g., toward a bone, may be accomplished while the locking mechanism 225 is in either the engaged position or the disengaged position. However, according to one or more aspects, moving the body 201 in the first direction, i.e., in the direction of the arrow 251, e.g., away from a bone, may be allowed only while the locking mechanism 225 is in the disengaged position.

As such, referring back to FIGS. 4A-4B, engaging the body 401 with the bone 421 may include moving the locking mechanism from an engaged position to a disengaged position and moving the body 401 toward the bone along the central axis 450 of the body 401. However, as discussed above, the locking mechanism may not necessarily need to be in the disengaged position in order to allow the body 401 to move along the central axis 450 of the body 401 toward the bone 421, i.e., in the second direction. For example, according to one or more aspects, the locking mechanism may be in the engaged position when the body 401 is moved, or displaced, toward the bone 421 and is engaged with the second side of the bone 401. As will be discussed below, according to one or more aspects, the locking mechanism may be moved from the engaged position to the disengaged position in order to release, or disengage, the guide apparatus 400 from the bone 421.

As discussed above, according to one or more aspects, the handle 405 may include a slot 406 formed thereon, in which at least a portion of the arm 402 may be engaged with the slot 406 and may be slidable within the slot 406. Further, as discussed above, the arm 402 may include a feature or mechanism that may lock the arm 402 within the slot 406 of the handle 405, or prevent relative movement of the arm 402 relative to the handle 405, in order to secure a position of the arm 402.

As shown, a bone 422 is shown disposed substantially adjacent to the bone 421, such as in a joint. According to one or more aspects, the bone 421 may be a tibia and the bone 422 may be a femur. However, those having ordinary skill in the art will appreciate that the bones 421, 422 may be any bone, including, but not limited to, a radius, an ulna, and a humerus.

Figure 5:
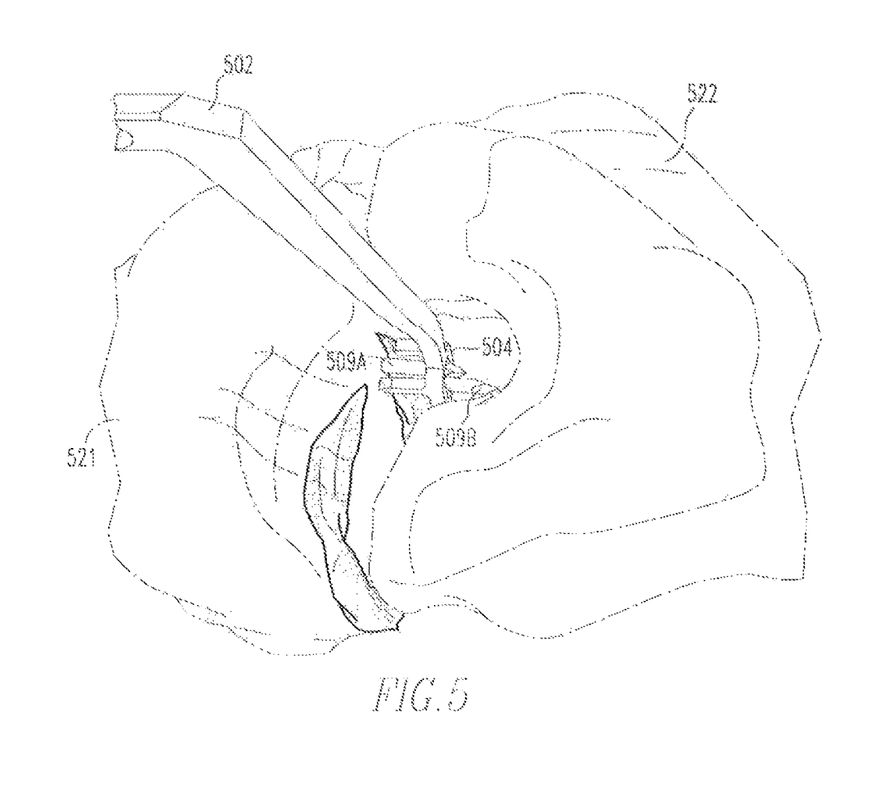
FIG. 5 is a close-up view of a guide apparatus engaged with a bone, in which guidewires are disposed through the bone and at least partially through a guide loop formed on a distal end of an arm of the guide apparatus, in accordance with embodiments disclosed herein.

According to one or more aspects, a distal end of the arm may include a guide loop configured to receive at least two guidewires. Referring to FIG. 5, a close-up view of a guide apparatus engaged with a bone 521, in which guidewires 509A, 509B are disposed through the bone 521 and at least partially through a guide loop 504 formed on a distal end of an arm 502 of the guide apparatus, in accordance with embodiments disclosed herein, is shown. As shown, the arm 502 includes the guide loop 504, in which a first guidewire 509A and a second guidewire 509B are at least partially disposed through the guide loop 504. Further, as shown, the guidewires 509A, 509B are disposed through a bone 521, but do not necessarily penetrate or engage a bone 522.

According to one or more aspects, the guidewires 509A, 509B may be drilled into the bone 521. According to one or more aspects, the guidewires 509A, 509B may be drilled through the bone 521. According to one or more aspects, drilling the guidewires 509A, 509B through the bone may include drilling the guidewires 509A, 509B through the bone 521, through the guide loop 504, until at least a portion of at least one of the guidewires 509A, 509B is disposed through the guide loop 504. Those having ordinary skill in the art will appreciate that the guidewires 509A, 509B may drilled through the bone 521, toward the guide loop 504, and may not necessarily need to be at least partially disposed through the guide loop 504. For example, according to one or more aspects, the guidewires 509A, 509B may be drilled through the bone 521, which may allow a substantially oval-shaped tunnel to be formed through the bone 521, without any portion of the guidewires 509A, 509B being disposed through the guide loop 504.

Those having ordinary skill in the art will appreciate that drilling the at least one guidewire, e.g., guidewires 509A, 509B into the bone 521 may include the use of any drilling tool known in the art and may not necessarily be limited to drilling. For example, a powered drilling tool may be used to drill the guidewires 509A, 509B into the bone 521. Alternatively, any other means known in the art may be used to drill, force, or otherwise dispose, the guidewires 509A, 509B into the bone 521.

As discussed above, the guide loop 504 may provide an intended target region, through which the guidewires 509A, 509B may be intended to be disposed. For example, as discussed above, the guide loop 504 of the arm 502 may be engaged with a first side of the bone 521, and at least a portion of a body (not shown) may be engaged with a second side of the bone 521. According to one or more aspects, the guidewires 509A, 509B may be disposed through channels (not shown) formed through the body, through the second side of the bone 521, through the bone 521, and may exit the first side of the bone 521 toward the guide loop 504 and may be at least partially disposed through the guide loop 504. As such, according to one or more aspects, the configuration of the arm 502 and the guide loop 504 may help precisely guide the guidewires 509A, 509B into, and through, a specific location of the bone 521. Accurately positioning the guidewires 509A, 509B, and through, a specific location of the bone 521 may allow a substantially oval-shaped tunnel to be formed through a specific location of the bone 521.

Figure 6:
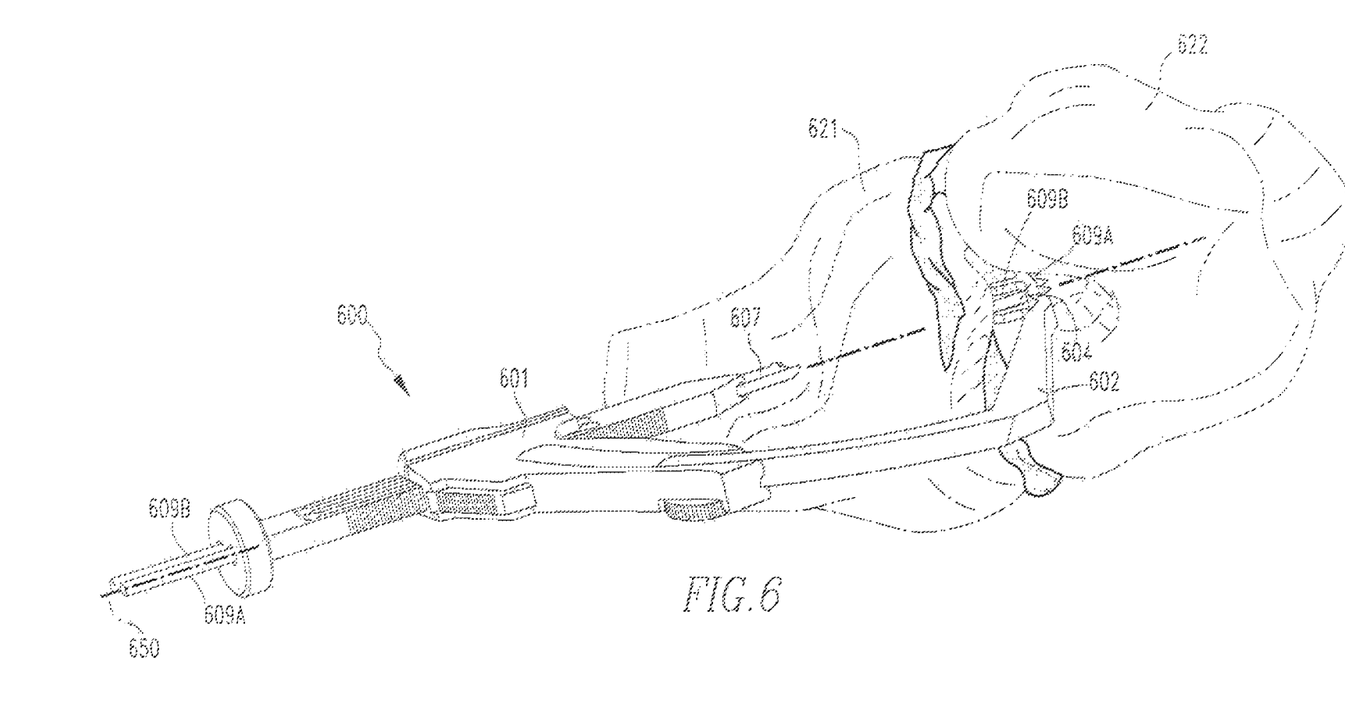
FIG. 6 is a perspective view of a guide apparatus engaged with a bone in which guidewires are disposed through the bone and at least partially through a guide loop formed on a distal end of an arm of the guide apparatus, in accordance with embodiments disclosed herein.

Referring to FIG. 6, a perspective view of a guide apparatus 600 engaged with a bone 621 in which guidewires 609A, 609B are disposed through the bone 621 and at least partially through a guide loop 604 formed on a distal end of an arm 602 of the guide apparatus 600, according to embodiments disclosed herein, is shown.

As discussed above, according to one or more aspects, the arm 602 of the guide apparatus 600 may be engaged with a first side of the bone 621. Further, as discussed above, according to one or more aspects, the body 601 may have a central axis 650 defined therethrough and may include a projection 607 that may be configured to engage with a second side of the bone 621.

According to one or more aspects, both the projection 607 and the distal end of the arm 602, e.g., a center of a guide loop (not shown) formed on the distal end of the arm 602, may be substantially aligned with the central axis 650 of the body 601. Further, as discussed above, a first channel (not shown) and a second channel (not shown) may be formed through the body 601 and may be configured to receive guidewires (not shown). According to one or more aspects, the first channel may be substantially parallel to the second channel and the channels may be formed on either side of the projection 607. This structure, or configuration, may allow guidewires to be guided in a direction that is substantially parallel to the central axis 650 of the body 601, toward the bone 621 and toward the distal end of the arm 602.

As discussed above, according to one or more aspects, engaging the body 601 with the bone 621 may include moving the locking mechanism from an engaged position into a disengaged position and moving the body 601 toward the bone 621, along the central axis 650 of the body 601, until at least a portion of the body 601 is engaged with the bone 601.

As such, engaging the body 601 with the bone 621 may include moving the locking mechanism from an engaged position to a disengaged position and moving the body 601 toward the bone along the central axis 650 of the body 601. However, as discussed above, the locking mechanism may not necessarily need to be in the disengaged position in order to allow the body 601 to move along the central axis 650 of the body 601 toward the bone 621, i.e., in the second direction. For example, according to one or more aspects, the locking mechanism may be in the engaged position when the body 601 is moved, or displaced, toward the bone 621 and is engaged with the second side of the bone 601.

According to one or more aspects, the locking mechanism may be moved from the engaged position to the disengaged position in order to release, or disengage, the guide apparatus 600 from the bone 621. For example, once the guidewires 609A, 609B are drilled, secured, or disposed through the bone 621, the guide apparatus 600 may be disengaged, or released, from the bone 621. In other words, each of the arm 602 and the body 601, e.g., the projection 607 of the body 601, may be disengaged from the bone 621 and the guide apparatus 600 may be removed.

For example, referring back to FIG. 2 described above, the trigger 211 may be moved, or displaced, in the second direction, i.e., in the direction of arrow 252, which may cause the locking portion 217 of the movable piece 213 to disengage from the locking threads 218 of the body 201. As discussed above, according to one or more aspects, once the locking portion 217 of the movable piece 213 is disengaged from the locking threads 218 of the body 201, the locking mechanism 225 is in the disengaged position. Once the locking mechanism 225 is in the disengaged position, the body 201 may be free to move in both the first direction and the second direction relative to the handle 205. According to one or more aspects, moving the body 201 in the first direction, i.e., in the direction of the arrow 251, e.g., away from a bone, may be allowed only while the locking mechanism 225 is in the disengaged position.

Referring back to FIG. 6, once the locking mechanism is in the disengaged position, the body 601 may be moved in a direction, relative to the handle 605, that is away from the bone 621 and may be disengaged from the bone 621. Further, the arm 602, e.g., the guide loop 604 or the one or more projections (not shown) of the arm 602, may be disengaged from the bone 621, and the guide apparatus 600 may be removed.

As shown, a bone 622 is shown disposed substantially adjacent to the bone 621, such as in a joint. As discussed above, according to one more aspects, the guidewires 609A, 609B may be disposed through a bone 621, but do not necessarily penetrate or engage the bone 622. According to one or more aspects, the bone 621 may be a tibia and the bone 622 may be a femur. However, those having ordinary skill in the art will appreciate that the bones 621, 622 may be any bone, including, but not limited to, a radius, an ulna, and a humerus.

According to one or more aspects, once the guidewires 609A, 609B are secured within the bone 621 and the guide apparatus 600 is disengaged from the bone 621 and removed, an oval shaped tunnel may be formed through the bone 621 using the guidewires 609A, 609B. For example, according to one or more aspects, a cannulated drill may be used to drill over each of the guidewires 609A, 609B and form holes through the bone 621. According to one or more aspects, the holes formed over the guidewires 609A, 609B by the cannulated drill may be overlapping holes and may form a substantially oval-shaped tunnel through the bone 621. Further, according to one or more aspects, a dilator may be used to help form an oval-shaped tunnel from the holes formed by the cannulated drill. Those having ordinary skill in the art will appreciate that any other means known in the art of forming a substantially oval-shaped using at least one guidewire known in the art may be used.

Advantageously, embodiments disclosed herein may provide a guide apparatus for precisely guiding at least one guidewire into a bone and accurately positioning at least one guidewire within the bone. The aspects of the invention, discussed above, may allow one or more guidewires to be precisely guided and accurately disposed within the bone, which may allow an oval-shaped tunnel to be formed through an exact portion of the bone, using the guidewires.

As discussed above, a placement of the ACL origin or insertion which is too anteriorly placed in the knee joint may result in a ligament that is taut in flexion, but lax in extension. Posterior placement may cause the ligament to be taut in extension, but lax in flexion. Only isometric placement may provide stability throughout the range of motion. As such, aspects of the invention, discussed above, may allow an oval-shaped tunnel to be formed through an exact portion of the bone, using the guidewires, which may allow more consistent isometric placement of an ACL ligament, or graft bundle, in ACL reconstructive surgical procedures.

While embodiments have been described with respect to a limited number of embodiments, those skilled in the art, having benefit of this disclosure, will appreciate that other embodiments can be devised which do not depart from the scope of embodiments disclosed herein. Accordingly, the scope of embodiments disclosed herein should be limited only by the attached claims.

What is claimed is:

1. A method of guiding at least one guidewire into a bone, comprising:
    providing a guide apparatus including a body, a handle coupled to the body, and an arm coupled to the handle, the body having a central axis, a projection, a first channel, and a second channel, the first channel and the second channel being configured to receive a first guidewire and a second guidewire, respectively, the projection being at least approximately aligned with the central axis of the body, the first channel and the second channel being at least approximately in parallel with each other on either side of the projection;
    engaging a bone with the projection of the body of the guide apparatus;
    engaging at least a portion of the bone with the arm of the guide apparatus;
    disposing the first guidewire and the second guidewire into the first channel and the second channel, respectively, of the body of the guide apparatus to allow the first guidewire and the second guidewire to be guided in a first direction toward the bone at least approximately parallel to the central axis of the body of the guide apparatus; and
    drilling one or both of the first guidewire and the second guidewire into the bone.

2. The method of claim 1, wherein the handle comprises a slot formed thereon, wherein a proximal end of the arm is engaged with the slot and is slidable within the slot and wherein a position of the arm relative to the handle is lockable within the slot.

3. The method of claim 1, wherein the handle includes a locking mechanism that, in an engaged position, prevents movement of the body relative to the handle in a first direction and allows movement of the body relative to the handle in a second direction opposite the first direction and in a disengaged position, allows the body to move relative to the handle in both the first direction and the second direction.

4. The method of claim 3, wherein each of the first direction and the second direction are along the central axis of the body.

5. The method of claim 3, wherein the locking mechanism comprises at least one biasing member configured to bias the locking mechanism toward the engaged position.

6. The method of claim 3, wherein engaging the body with the bone comprises moving the locking mechanism from the engaged position into the disengaged position and moving the body toward the bone, along the central axis of the body, until at least a portion of the body is engaged with the bone.

7. The method of claim 1, wherein a distal end of the arm comprises a guide loop configured to receive the guidewires.

8. The method of claim 7, wherein the guide loop includes at least one protrusion, and wherein engaging the arm with the bone comprises engaging the at least one protrusion with the bone.

9. The method of claim 7, wherein drilling one or both of the guidewires into the bone comprises drilling the one or both of the guidewires through the bone and through the guide loop positioned on an opposite side of the bone, whereby at least a portion of the one or both of the guidewires is disposed through the guide loop.

10. The method of claim 7, wherein a geometric projection of a shape of the guide loop into a plane perpendicular to the central axis of the body is oval shaped or otherwise elongated.

11. The method of claim 1 wherein drilling the first guidewire and the second guidewire into the bone comprises drilling the first guidewire and the second guidewire through the bone and through a guide loop positioned on an opposite side of the bone whereby at least a portion of one or more of the first guidewire and the second guidewire are disposed in the guide loop.

12. The method of claim 11, further comprising forming a tunnel through the bone, wherein forming the tunnel through the bone includes drilling over each of the first and second guidewires.

13. The method of claim 12, wherein the forming the tunnel through the bone includes forming overlapping holes through the bone by drilling over the first and second guidewires.

14. The method of claim 12, wherein the forming the tunnel through the bone includes using a dilator to further form the tunnel after drilling over each of the first and second guidewires.

15. The method of claim 12, wherein the tunnel is oval-shaped or otherwise elongated.

* * * * *